United States Patent
Murakami et al.

(10) Patent No.: US 6,762,171 B1
(45) Date of Patent: Jul. 13, 2004

(54) FATTY ACID COA THIOESTER INHIBITORY SUBSTANCE OF PPARα AND PPARγ

(75) Inventors: Koji Murakami, Tochigi (JP); Tomohiro Ide, Ibaragi (JP); Toshiro Mochizuki, Saitama (JP); Takashi Kadowaki, Kanagawa (JP)

(73) Assignee: Kyorin Pharmaceutical Co, Ltd., Tokyo (JP)

(*) Notice: Subject to any disclaimer, the term of this patent is extended or adjusted under 35 U.S.C. 154(b) by 0 days.

(21) Appl. No.: 10/070,439

(22) PCT Filed: Sep. 24, 1999

(86) PCT No.: PCT/JP99/05217

§ 371 (c)(1),
(2), (4) Date: May 30, 2002

(87) PCT Pub. No.: WO01/21181

PCT Pub. Date: Mar. 29, 2001

(51) Int. Cl.[7] ............................................ C07H 19/207
(52) U.S. Cl. ...................................... 514/47; 536/26.23
(58) Field of Search ......................... 536/26.23; 514/47

(56) References Cited

FOREIGN PATENT DOCUMENTS

| WO | WO 91/00871 | 1/1991 |
|----|-------------|--------|
| WO | WO 97/10813 | 3/1997 |
| WO | WO 98/51296 | 11/1998 |

OTHER PUBLICATIONS

Sigma Chemical Company, catalog, 1989, St. Louis, MO., pp. 448–450.*
Hertz, Rachel; Magenheim, Judith; Berman, Inna; Bar–Tana, Jacob, Nature (London), 392(6675), 512–516 (English) 1998.*
Elholm,Morten; et al Journal of Biological Chemistry, 276(24), 21410–21416, (English) 2001.r.*
Eric Weisstein "World of Science" [online] Wolfram Research, [retreived on Oct. 4, 2003], Retreived from the Internet, <http://scienceworld.wolfram.com/chemistry/FattyAcid.html>.*
Kane K, "Biochemistry, 3rd Ed.", Wm. C. Brown, Dubuque, IA, 1993.*
Nuss, J.M. et al, in "Ann. Reports Med. Chem. vol. 35", 2000, Academic Press, San Diego, p 211–220.*
Nordlie, Robert C.; Hanson, Thomas Lawrence; Johns, Philip T., Journal of Biological Chemistry, 242(18), 4144–8 (English) 1967.*
Jennifer L. Oberfield, et al. "A peroxisome proliferator–activated receptor y ligand inhibits adipocyte defferentiation" Proc. Natl. Acad. Sci. USA, vol. 96, pp. 6102–6106, 05/99.
J. Vamecq, et al., The Lancet, vol. 354, No. 9173, XP–004266618, pp. 141–148, "Medical Significance of Peroxisome Proliferator–Activated Receptors", Jul. 10, 1999.

* cited by examiner

Primary Examiner—Mukund J. Shah
Assistant Examiner—Tom McKenzie
(74) Attorney, Agent, or Firm—Oblon, Spivak, McClelland, Maier & Neustadt, P.C.

(57) ABSTRACT

The invention creates a very high-novelty medicinal drug for the carbohydrate and lipid metabolism-related diseases by finding out an inhibitory substance or antagonist against PPAR α and PPAR γ, and relates to an application of fatty acid CoA thioester that was found out as an active inhibitory substance against peroxisome proliferator-activated receptor α and γ (hereinafter referred to as PPARs) to the assay of medicinal drug, and a use of fatty acid CoA thioester for medicinal drug.

16 Claims, No Drawings

FATTY ACID COA THIOESTER INHIBITORY SUBSTANCE OF PPARα AND PPARγ

TECHNICAL FIELD

The present invention relates to an application of fatty acid CoA thioester found out as an active inhibitory substance against peroxisome proliferator-activated receptor α and γ (hereinafter referred to as PPARs) to the assay of medicinal drug, and a use of fatty acid CoA thioester for medicinal drug.

BACKGROUND TECHNOLOGIES

The peroxisome proliferator-activated receptor (PPAR) is a transcription factor to be activated when a ligand binds to the ligand-binding domain at the side of C-termini, and one of the nuclear receptor superfamily having glucocorticoid, estrogen, thyroxine and vitamin D as ligands (Keller H. et al: Trends Endocrinol. Metab. (1993) 4, 291–296). So far, three types of isoforms of α form, γ form and δ form have been identified as PPARs, and the expression tissues and the functions are different respectively (Braissant O. et al: Endocrinology (1996) 137, 354–366). The PPAR α is highly expressed in the tissues with high catabolic activity of fatty acids such as liver, kidney and heart. The PPAR γ is divided into PPAR γ 1 and PPAR γ 2 as two types of isoforms with the sides of different N-termini through the selection of promoters; PPAR γ 1 is expressed in the relatively widespread tissues and PPAR γ 2 is highly expressed mainly in the adipose tissue. The PPAR δ is distributed in the widespread tissues.

The PPAR α binds to promoter domain of key enzymes concerning in the lipid catabolism system such as acyl-CoA synthase existing in the cytosol, acyl-CoA dehydrogenase and HMG-CoA synthase existing in the mitochondria and acyl-CoA oxidase existing in the peroxisome of liver (Schoonjans K. et al: J. Lipid Res.(1996) 37, 907–925). From the analysis of PPAR α-deficient mice, it is being considered that the PPAR α plays an important role for the energy acquisition in starvation state, that is, oxidation of fatty acid and formation of ketone body in liver (Kersten S. et al: J. Clin. Invest. (1999) 103, 1489–1498).

On the other hand, it is known that the PPAR γ concerns deeply in the differentiation of adipocytes (Forman BM. et al: Cell (1995) 83, 803–812). Thiazolidinedione derivatives such as troglitazone, rosiglitazone (BRL-49,653) and pioglitazone are new therapeutic drugs of type 2 diabetes with a unique function that improves the insulin resistance being one of pathogenic factors of diabetes, and, in recent years, it has been revealed that those drugs are agonists against PPAR γ (Lehmann JM. et al: J. Biol. Chem. (1995) 270, 12953–12956). It is being considered that the PPAR γ plays an important role for the energy storage in organisms. However, the function of PPAR δ is not very understood compared with α form or γ form.

As described above, for the agonists against PPAR, glitazone-classed drugs are well known. Also, it is reported that natural or endogenous-produced saturated and unsaturated fatty acids, certain kinds of eicosanoid, oxidized fatty acids, etc. are agonists against PPAR (Forman BM. et al: Proc. Natl. Acad. Sci. USA (1997) 94, 4312–4317).

On the other hand, it is the status quo that the inhibitory substance and antagonist against PPAR are little known. Only 2,4-thiazolidinedione derivatives are known as the antagonists against PPAR γ (Oberfield J. L. et al; Proc. Natl. Acad. Sci. USA (1999) 96, 6102–6106).

As the use of antagonist against PPAR γ, application to antiobesity drug is disclosed (WO97/10813), not getting however to the discovery of antagonistic substance.

Much less, the inhibitory substance or antagonist against PPAR α is not known at all.

Up to this time, no antagonist against PPAR γ and PPAR α has been discovered even in the natural or endogenous substances.

The purpose of the invention is to create a very high-novelty medicinal drug for the carbohydrate and lipid metabolism-related diseases by finding out an inhibitory substance or antagonist against PPAR α and PPAR γ.

DISCLOSURE OF THE INVENTION

When the inventors were implementing studies on the participation of PPAR in the induction of insulin resistance, they have found, to their surprise, that certain fatty acid CoA thioester forms being the metabolites of fatty acids have inhibitory function against PPAR α and PPAR γ, leading to the completion of the invention.

Namely, through competition binding experiments using tritium-labeled form of KRP-297 (Murakami K. et al: Diabetes (1998) 47, 1841–1847) being a dual agonist against PPAR α and PPAR γ, it has been found that different fatty acid CoA thioesters bind well to the ligand-binding domains of PPAR α and PPAR γ, thus making it clear that they are ligands of both α and γ receptors.

In addition, the fatty acid CoA thioesters dose-dependently inhibited the binding activity on the conjugate formation between ligand-binding domains of PPAR α and PPAR γ and steroid receptor coactivator (SRC-1). Consequently, the fatty acid CoA thioesters clarified themselves to be inhibitory substances of PPAR α and PPAR γ.

According to the invention, the fatty acid CoA thioester can be used for the exploration of creation of medicinal drug and the assay tools, as an inhibitory substance or antagonist against PPAR α and PPAR γ, which makes it useful.

Namely, the fatty acid CoA thioester in which fatty acid group is myristoyl, palmitoyl, stearoyl, oleoyl, linoleoyl or arachidonoyl can be used for the creation of medicinal drug as an inhibitory substance against PPAR α, and the fatty acid CoA thioester in which fatty acid group is myristoyl, palmitoyl, stearoyl, oleoyl, linoleoyl or arachidonoyl can be used for the creation of medicinal drug as an inhibitory substance against PPAR γ.

Furthermore, it is also possible to use the fatty acid CoA thioester itself as a medicinal drug. Fields of medicinal drug are as follows:

1) Application as an Antagonist of PPAR α

It is known that, in the case of critical diabetes, mainly type 1 diabetes, the diabetic ketoacidosis can often occur as an acute complication. The diabetic ketoacidosis clinically assumes dehydration, disorder of consciousness, depressed blood pressure, tackycardia, respiratory stimulation, Kussmaul's large respiration and acetone odor of exhalation (Keller U. et al: Diabetologia (1986) 29, 7–77). From the fact that PPAR α plays an important role for the oxidation of fatty acid and the formation of ketone body in liver, it is expected that the antagonist of PPAR α can inhibit them, hence it is useful for the therapy of diabetic ketoacidosis.

2) Application as an Antagonist of PPAR γ

Obesity is a risk factor for diabetes, hyperlipidemia, hypertension, ischemic heart disease, etc., hence the prevention and therapy thereof are very important subjects clinically. The PPAR γ plays an important role for the differentiation of adipocytes. Actually, the thiazolidinedione derivatives, PPAR γ agonists, have differentiation-inducing function of adipocytes, and it is reported that they increase the number of adipocytes and the weight of adipose tissue (Piet De Vos et al: J. Clin. Invest. (1996) 98, 1004–1009). While the thiazolidinedione derivatives have usefulness as the therapeutic drugs of diabetes, they induce the differentiation of adipocytes, hence the potential for promoting the obesity is also feared. Also, it is reported that the expression level of leptin known as an antiobese factor is deprssed through the administration of thiazolidinedione derivatives (Zhang E. et al: J. Biol. Chem. (1996) 271, 9455–9459). Based on these backgrounds, the antagonist of PPAR γ suppresses the differentiation of adipocytes and, at the same time, it increases the expression level of leptin, thereby the potential as an antiobesity drug is expected.

BEST EMBODIMENT TO PUT THE INVENTION INTO PRACTICE

In following, the invention will be illustrated based on concrete examples, but the invention is not confined to these examples.

EXAMPLE 1

Measurement of Binding Activity to PPAR α and PPAR γ

Competition experiments using tritium-labeled form of KRP-297 (Murakami K. et al: Diabetes (1998) 47, 1841–1847) being a dual agonist against PPAR α and PPAR γ were implemented. Proteins (6×His-hPPARs LBD) tagged 6-copy histidine to the side of N-termini in the ligand-binding domains of human-type PPAR α and PPAR γ were expressed in *Escherichia coli*, respectively, and purified through a nickel column. 6×His-hPPARs LBD protein and 100 nM [3H]KRP-297 (27Ci/mmol) were incubated for 30 minutes at 25° C. in 50 mM Tris-HCl buffer (pH 7.4) containing 50 mM KCl and 10 mM dithiothreitol in the presence or absence of testing compound (fatty acid CoA thioester, from Sigma Co.). Thereafter, [$^3$H]KRP-297 bound to protein was separated through Sephadex G25 column and the radioactivity was measured with liquid scintillation counter.

As control drugs for the binding activity against PPAR γ, BRL-49,653 (Willson TM. et al: J. Med. Chem. (1996) 39, 665–668) and 15-deoxy- $\Delta^{12,14}$-prostaglandin J$_2$ (from Cayman Chemical Co.) were used and, as a control drug for the binding activity against PPAR α, 8(S)-hydroxyeicosatetraenoic acid (from Cayman Chemical Co.) was used.

As a result, it became clear that the thioester of myristic acid CoA, palmitic acid CoA, stearic acid CoA, oleic acid CoA, linoleic acid CoA or arachidonic acid CoA was ligand of PPAR α and PPAR γ (Table 1).

TABLE 1

Binding of fatty acid CoA to the ligand-binding domain of PPAR

|  | PPARα | PPARγ |
|---|---|---|
| BRL-49,653 |  | 99% |
| 15-Deoxy-$\Delta^{12,14}$-prostaglandin J$_2$ |  | 93% |
| 8(S)-Hydroxyeicosatetraenoic acid | 99% |  |

TABLE 1-continued

Binding of fatty acid CoA to the ligand-binding domain of PPAR

|  | PPARα | PPARγ |
|---|---|---|
| Myristoyl CoA | 70% | 45% |
| Palmitoyl CoA | 83% | 72% |
| Stearoyl CoA | 94% | 89% |
| Oleoyl CoA | 95% | 52% |
| Linoleoyl CoA | 92% | 59% |
| Arachidonoyl CoA | 54% | 46% |

Data represent average value of 3 experiments± standard error.

EXAMPLE 2

Measurement of Conjugate-Forming Activity Between PPARs LBD and SRC-1

[35S]methionine-labeled form of SRC-1 containing 2-copy of LXXLL motif was prepared in vitro (TNTR, Promega Co., Madison, Wis.). 6×His-hPPARs LBD protein was incubated for 60 minutes at 4° C. in 50 mM Tris-HCl buffer (pH 7.4) containing 50 mM KCl and 1 mM dithiothreitol and 0.1% bovine serum albumin in the presence or absence of testing compound. Thereafter, 2 mg of anti-6×His antibody (QIAGEN Co., Germany) were added and the mixture was incubated for 60 minutes at 4° C. Successively, 20 ml of protein G Sepharose (Falmasia Biotech Co., Sweden) were added and the mixture was incubated for 60 minutes at 4° C. After washed thrice by centrifugation, protein G Sepharose was dissolved with 20 ml of SDS-sample buffer, 20% SDS-PAGE, and then [35S]SRC-1 was detected by means of autography.

As a result, linoleic acid CoA thioester dose-dependently inhibited the conjugate formations of SRC-1 due to ligands of PPAR α, KRP-297 and linoleic acid, and also dose-dependently inhibited the conjugate formations of SRC-1 due to ligands of PPAR γ, BRL-49,653 and linoleic acid (Table 2).

TABLE 2

Inhibition of fatty acid CoA on the conjugate formation between PPARs ligand-binding domain and SRC-1

|  |  | Human PPARα KRP-297 | | Human PPARγ BRL-49653 | |
|---|---|---|---|---|---|
|  |  |  | linoleic acid |  | linoleic acid |
|  |  | 30 μM | 30 μM | 30 μM | 30 μM |
| Linoleoyl CoA | 0 μM | 6.1 ± 1.7 | 5.3 ± 1.9 | 4.8 ± 0.7 | 4.5 ± 0.7 |
| Linoleoyl CoA | 3 μM | 5.5 ± 1.5 | 6.1 ± 2.2 | 4.9 ± 0.6 | 4.2 ± 0.3 |
| Linoleoyl CoA | 10 μM | 4.4 ± 0.8 | 2.4 ± 0.8 | 4.8 ± 1.9 | 2.7 ± 1.1 |
| Linoleoyl CoA | 30 μM | 1.4 ± 0.1 | 1.2 ± 0.4 | 1.5 ± 0.5 | 1.9 ± 0.8 |
| Linoleoyl CoA | 100 μM | 0.9 ± 0.3 | 0.9 ± 0.3 | 1.0 ± 0.1 | 1.3 ± 0.4 |

Data represent average value of 3 experiments± standard error.

Utilizability in the Industry

When studies on the participation of PPAR in the induction of insulin resistance were implemented, it was found that certain fatty acid CoA thioester forms being the metabolites of fatty acids had inhibitory function against PPAR α and PPAR γ.

As a result, the fatty acid CoA thioester in which fatty acid group is myristoyl, palmitoyl, stearoyl, oleoyl, linoleoyl or arachidonoyl can be used for the creation of medicinal drug as an inhibitory substance against PPAR α, and the fatty acid CoA thioester in which fatty acid group is myristoyl, palmitoyl, stearoyl, oleoyl, linoleoyl or arachidonoyl can be used for the creation of medicinal drug as an inhibitory substance against PPAR γ.

Furthermore, it is also possible to use the fatty acid CoA thioester itself as a medicinal drug concerning in the carbohydrate and lipid metabolism-related diseases.

What is claimed is:

1. A method of inhibiting PPAR α in an individual, comprising administering a fatty acid CoA thioester to the individual in an amount sufficient to inhibit PPARα.

2. The method of claim 1, wherein the fatty acid group of the fatty acid CoA thioester is selected from the group consisting of myristoyl, palmitoyl, stearoyl, oleoyl, linoleoyl, and arachidonoyl.

3. The method of claim 2, wherein the fatty acid group of the fatty acid CoA thioester is myristoyl.

4. The method of claim 2, wherein the fatty acid group of the fatty acid CoA thioester is palmitoyl.

5. The method of claim 2, wherein the fatty acid group of the fatty acid CoA thioester is stearoyl.

6. The method of claim 2, wherein the fatty acid group of the fatty acid CoA thioester is oleoyl.

7. The method of claim 2, wherein the fatty acid group of the fatty acid CoA thioester is linoleoyl.

8. The method of claim 2, wherein the fatty acid group of the fatty acid CoA thioester is arachidonoyl.

9. A method of inhibiting PPAR γ an individual, comprising administering a fatty acid CoA thioester to the individual in an amount sufficient to inhibit PPARγ.

10. The method of claim 9, wherein the fatty acid group of the fatty acid CoA thioester is selected from the group consisting of myristoyl, palmitoyl, stearoyl, oleoyl, linoleoyl, and arachidonoyl.

11. The method of claim 10, wherein the fatty acid group of the fatty acid CoA thioester is myristoyl.

12. The method of claim 10, wherein the fatty acid group of the fatty acid CoA thioester is palmitoyl.

13. The method of claim 10, wherein the fatty acid group of the fatty acid CoA thioester is stearoyl.

14. The method of claim 10, wherein the fatty acid group of the fatty acid CoA thioester is oleoyl.

15. The method of claim 10, wherein the fatty acid group of the fatty acid CoA thioester is linoleoyl.

16. The method of claim 10, wherein the fatty acid group of the fatty acid CoA thioester is arachidonoyl.

* * * * *